(12) United States Patent
Chang (10) Patent No.: US 8,795,216 B2
(45) Date of Patent: Aug. 5, 2014

(54) WAIST SUPPORT WITH DISC PROTECTION BELT

(76) Inventor: Ki Yong Chang, Seoul (KR)

( * ) Notice: Subject to any disclaimer, the term of this patent is extended or adjusted under 35 U.S.C. 154(b) by 171 days.

(21) Appl. No.: 13/584,095

(22) Filed: Aug. 13, 2012

(65) Prior Publication Data

US 2013/0144198 A1    Jun. 6, 2013

(30) Foreign Application Priority Data

Dec. 2, 2011    (KR) .................. 10-2011-0128327

(51) Int. Cl.
*A61F 5/02*    (2006.01)

(52) U.S. Cl.
USPC ............................................. 602/19; 128/876

(58) Field of Classification Search
CPC ........... A61F 5/02; A61F 5/022; A61F 5/024; A61F 5/026; A61F 5/028; A61H 1/008; A61H 2201/1623; A61H 2201/1626; A61H 2205/081
USPC ............... 602/19, 12; 128/96.1, 100.1, 101.1, 128/102.1, 876; 2/44, 311
See application file for complete search history.

(56) References Cited

U.S. PATENT DOCUMENTS

| 5,433,697 | A  | * | 7/1995  | Cox ................................ 602/19 |
| 5,547,462 | A  | * | 8/1996  | Lanigan et al. ................. 602/19 |
| 5,690,609 | A  | * | 11/1997 | Heinze, III ...................... 602/19 |
| 6,099,490 | A  | * | 8/2000  | Turtzo ............................. 602/19 |
| 6,311,346 | B1 | * | 11/2001 | Goldman ...................... 5/81.1 T |
| 6,322,529 | B1 | * | 11/2001 | Chung ............................ 602/19 |
| 6,666,838 | B2 | * | 12/2003 | Modglin et al. ................ 602/19 |
| 7,329,231 | B2 | * | 2/2008  | Frank .............................. 602/19 |
| 8,142,380 | B2 |   | 3/2012  | Hasegawa |
| 2003/0199799 | A1 | * | 10/2003 | Modglin et al. ................ 602/19 |
| 2008/0234617 | A1 |   | 9/2008  | Lee et al. |
| 2011/0295169 | A1 | * | 12/2011 | Hendricks ....................... 602/19 |

FOREIGN PATENT DOCUMENTS

JP    4317257 B2    8/2009

* cited by examiner

*Primary Examiner* — Patricia Bianco
*Assistant Examiner* — Kari Petrik
(74) *Attorney, Agent, or Firm* — David S. Resnick; David F. Crosby (57) ABSTRACT

Provided is a waist support with a disc protection belt having functions of strongly pulling and fixing the backbone as well as extending the backbone.

4 Claims, 8 Drawing Sheets

WAIST SUPPORT WITH DISC PROTECTION BELT

CROSS-REFERENCE TO RELATED APPLICATION

This application is based upon and claims the benefit of priority from Korean Patent Application No. 10-2011-0128327, filed on Dec. 2, 2011, the contents of which are incorporated herein by reference in its entirety.

BACKGROUND

1. Field of the Invention

The present invention relates to a waist support with a disc protection belt, and particularly, to a waist support with a disc protection belt having functions of strongly pulling and fixing the backbone as well as extending the backbone.

2. Discussion of Related Art

In related art, a disc protection belt configured to expand by injection of air in a vertical direction and extend the backbone in order to cure discs or protect the waist is already known. Such a disc protection belt is provided for disc treatment to cure backache and unusual symptoms of the waist.

However, when the above-mentioned disc protection belt is used, while the backbone can be extended, it cannot be strongly compressed, pulled and fixed. That is, in the case of a patient who just underwent waist surgery or who has a weak backbone, it is necessary to strongly compress, pull and fix the backbone but a conventional disc protection belt is unable to do this.

SUMMARY OF THE INVENTION

In order to solve these problems, the present invention provides a waist support with a disc protection belt having functions of strongly pulling and fixing the backbone as well as extending the backbone.

In order to accomplish the object, the present invention is directed to a waist support with a disc protection belt formed to conform to the waist of the human body, which includes a panel formed to conform to the waist of the human body, and a disc protection belt coupled to the panel by a bolt, wherein the panel includes a support section disposed to correspond to the backbone, a bolt hole formed in the support section to be coupled to the disc protection belt by a bolt, and a pair of first openings formed in left and right sides of the support section, a pair of second openings spaced out a predetermined distance from the bolt hole with the first openings interposed therebetween, the disc protection belt is coupled to the panel through the bolt hole from outside the panel, and both ends of the disc protection belt enter the panel through the pair of first openings and then exit the panel through the pair of second openings.

In addition, in the waist support with a disc protection belt according to the present invention, a width of the support section may be gradually reduced toward a center thereof and the bolt hole may be formed in the center of the support section.

Further, in the waist support with a disc protection belt according to the present invention, the panel may further include a pair of third openings disposed between the pair of first openings and the pair of second openings.

Furthermore, in the waist support with a disc protection belt according to the present invention, the third openings may have center portions narrower than upper and lower portions thereof.

In addition, in the waist support with a disc protection belt according to the present invention, the panel may have an outside formed of an acrylonitrile butadiene styrene (ABS) material and an inside formed of a polyethylene (PE) or sponge material.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DETAILED DESCRIPTION OF EXAMPLE EMBODIMENTS

Hereinafter, exemplary embodiments of the present invention will be described in detail. However, the present invention is not limited to the embodiments disclosed below but can be implemented in various forms. The following embodiments are described in order to enable those of ordinary skill in the art to embody and work the present invention. To clearly describe the present invention, parts not relating to the description are omitted from the drawings. Like numerals refer to like elements throughout the description of the drawings. Therefore, the present invention should not be construed as limited to the embodiments set forth herein and may be embodied in different forms. As used herein, the singular forms "a", "an" and "the" are intended to include the plural forms as well, unless the context clearly indicates otherwise. It will be further understood that the terms "comprises" and/or "comprising," when used in this specification, specify the presence of stated components, motions, and/or devices, but do not preclude the presence or addition of one or more other components, motions, and/or devices thereof.

Figure 1:
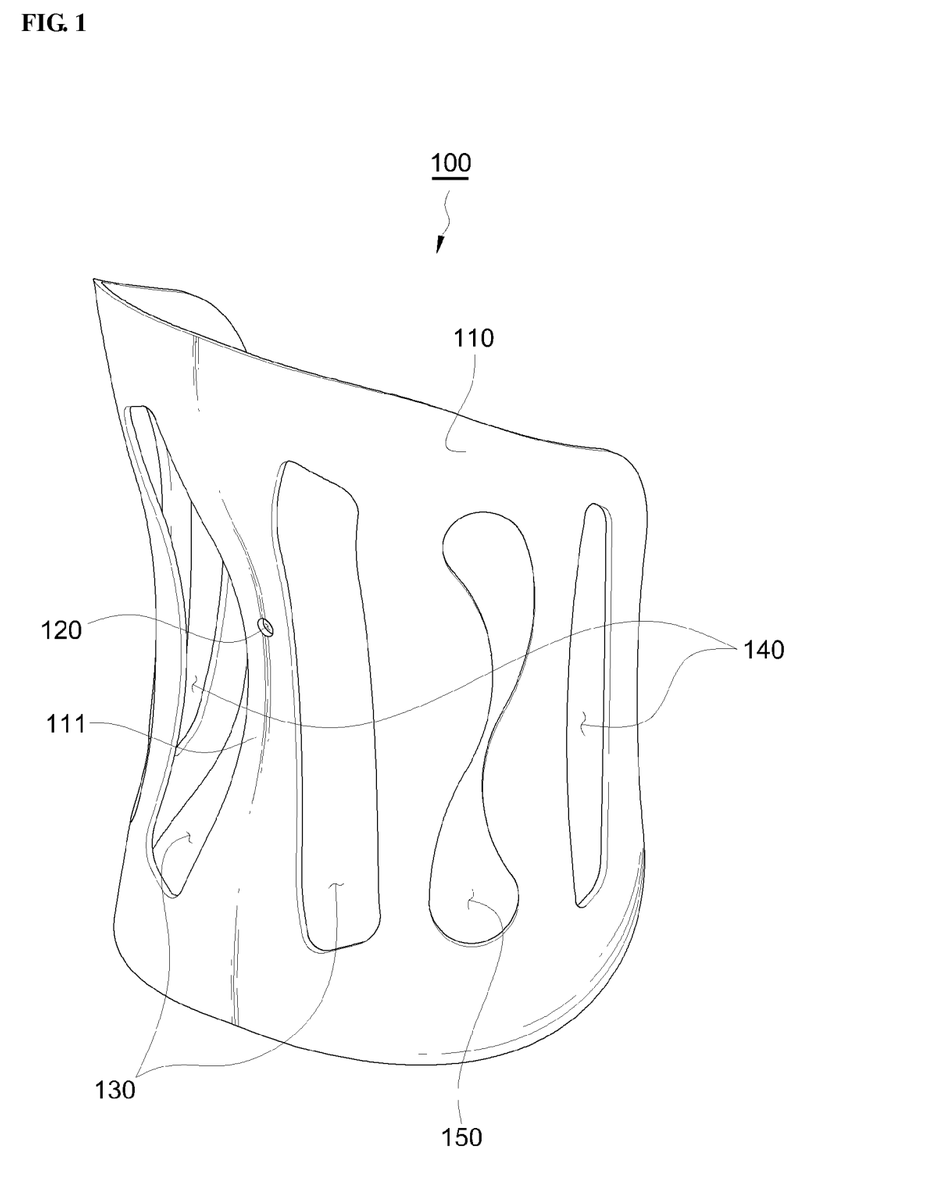
FIG. 1 is a perspective view showing a waist support of the present invention.
Figure 2:
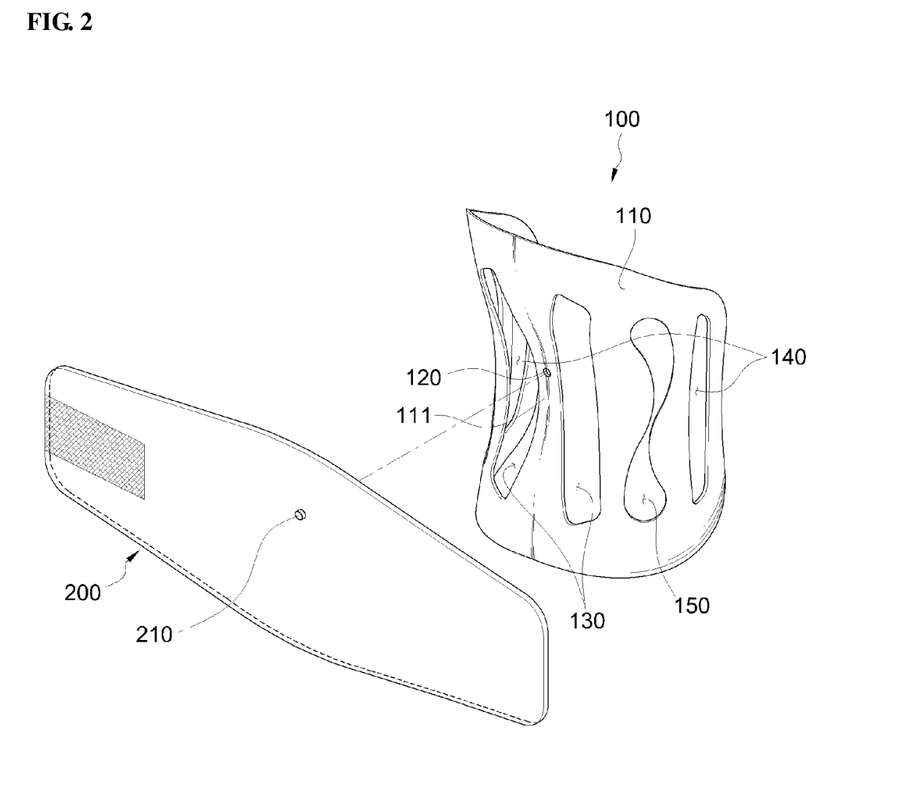
FIG. 2 is an exploded perspective view of a waist support with a disc protection belt according to an embodiment of the present invention.
Figure 3:
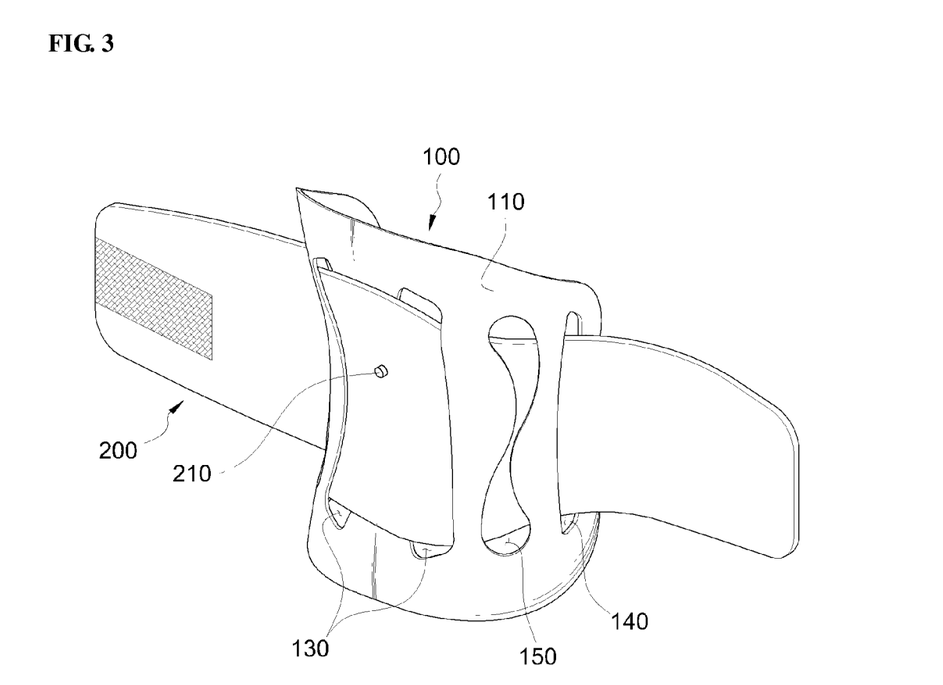
FIG. 3 is an assembled perspective view of the waist support with a disc protection belt according to the embodiment of the present invention.

FIG. 1 is a perspective view showing a waist support of the present invention, FIG. 2 is an exploded perspective view of a waist support with a disc protection belt according to an embodiment of the present invention, and FIG. 3 is an assembled perspective view of the waist support with a disc protection belt according to the embodiment of the present invention.

Referring to FIG. 1, a waist support 100 according to the present invention includes a panel 110 formed to conform to the waist of the human body 300. The panel 110 includes a support section 111 disposed to correspond to the backbone, a bolt hole 120 formed at a center of the support section 111 to be bolted to a disc protection belt 200 by a bolt 210, a pair of first openings 130 spaced out a predetermined distance from each other with the bolt hole 120 interposed therebetween, and a pair of second openings 140 spaced out a predetermined distance from the bolt hole 120 with the first openings 130 interposed therebetween.

In addition, the disc protection belt 200 is coupled to the panel 110 via the bolt hole 120 from outside the panel 110, and both ends of the disc protection belt 200 enter the panel 110 through the pair of first openings 130 and then exit the panel 110 through the pair of second openings 140.

As described above, since the waist support 100 according to the present invention includes the bolt hole 120, the first openings 130, and the second openings 140, which are formed in the panel 110, the disc protection belt 200 can be easily coupled to the panel 110 through the first openings 130 and the second openings 140.

In addition, since the waist support 100 according to the present invention has the support section 111 with the bolt hole 120 corresponding to the backbone of the human body 300, when the waist is pulled after the disc protection belt 200 is provided, the backbone can be more strongly pulled and fixed.

Further, in the waist support 100 according to the present invention, a width of the support section 111 is gradually reduced toward a center thereof, and the bolt hole 120 is formed at the center of the support section 111.

Accordingly, since the width of the support section 111 corresponding to the backbone of the human body 300 is gradually reduced to the center and the bolt hole 120 is formed at the center of the support section 111, the support section 111 has elasticity such that an upper portion and a lower portion of the support section 111 are bent into a C shape. As the upper and lower portions of the support section 111 are strongly compressed against the backbone by the elasticity to pull and fix the backbone, an incorrect backbone curve of the human body 300 can be corrected to a correct backbone curve (C shape).

Next, referring to FIGS. 2 and 3, the disc protection belt 200 is coupled to the panel 110 having the bolt hole 120 configured to couple the panel 110 to the disc protection belt 200 using the bolt 210, the pair of first openings 130 spaced out a predetermined distance from each other with the bolt hole 120 interposed therebetween, and the pair of second openings 140 spaced out a predetermined distance from the bolt hole 120 with the first openings 130 interposed therebetween.

The disc protection belt 200 is coupled to the panel 110 via the bolt hole 120 from outside the panel 110, and both ends of the disc protection belt 200 enter the panel 110 through the pair of first openings 130 and then exit the panel 110 through the pair of second openings 140.

As described above, the disc protection belt 200 according to the present invention can be coupled to the panel 110 through the bolt hole 120 to strongly pull the waist of the human body 300 from outside the panel 110.

Meanwhile, in the waist support 100 according to the present invention, the panel 110 may include a pair of third openings 150 formed between the pair of first openings 130 and the pair of second openings 140, and each center portion of the third openings 150 may be narrower than upper and lower portions thereof.

For example, as shown in FIGS. 2 and 3, in the case in which the third openings 150 have an "8" shape and are formed to pass through the panel 110, when the disc protection belt 200 is coupled to the panel 110 through the bolt hole 120 to strongly pull the waist of the human body 300 from outside the panel 110, a portion of the panel 110 having the bolt hole 120 and corresponding to the backbone of the human body 300 strongly compresses the backbone of the human body 300, and side portions of the waist of the human body 300 are compressed by the third openings 150 having the "8" shape of the panel 110 between the first openings 130 and the third openings 150, pulling the waist of the human body 300.

In addition, in the waist support 100 according to the present invention, the panel 110 has an outside formed of an acrylonitrile butadiene styrene (ABS) material and an inside formed of a polyethylene (PE) or sponge material.

As described above, since the inside of the panel 110 in direct contact with the waist of the human body 300 is formed of a PE or sponge material, the waist of the human body 300 can be pulled without causing awkward feeling, and as the outside of the panel 110 is formed of an ABS material having rigidity, deformation of the panel 110 can be prevented.

Figure 4:
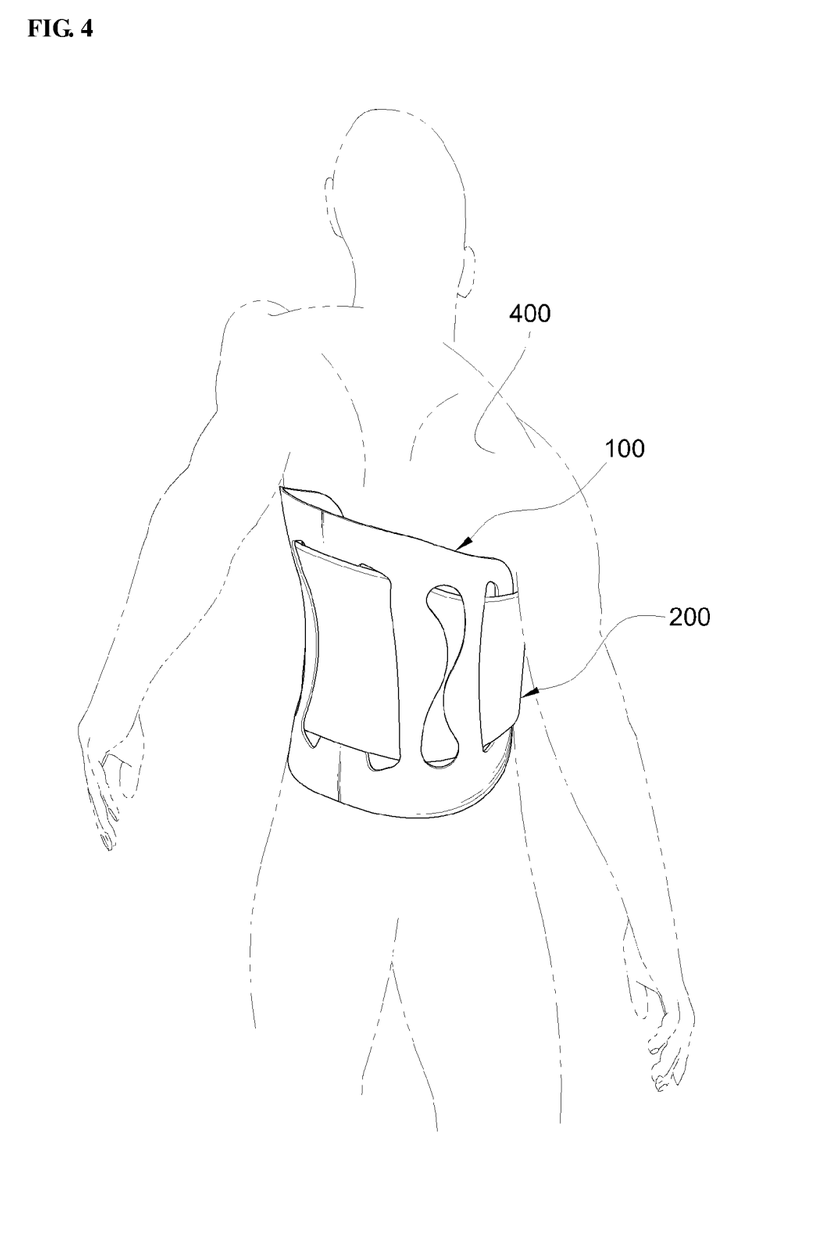
FIG. 4 is a view showing a state in which the waist support with a disc protection belt according to the embodiment of the present invention is worn on the human body.
Figure 5:
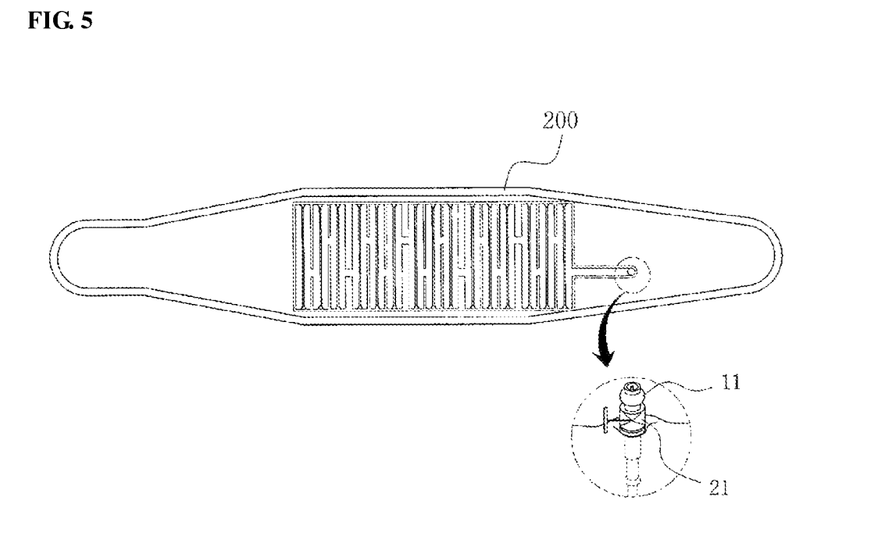
FIG. 5 is a schematic view showing a configuration in which an air control valve is installed at a disc protection belt of the present invention.
Figure 6:
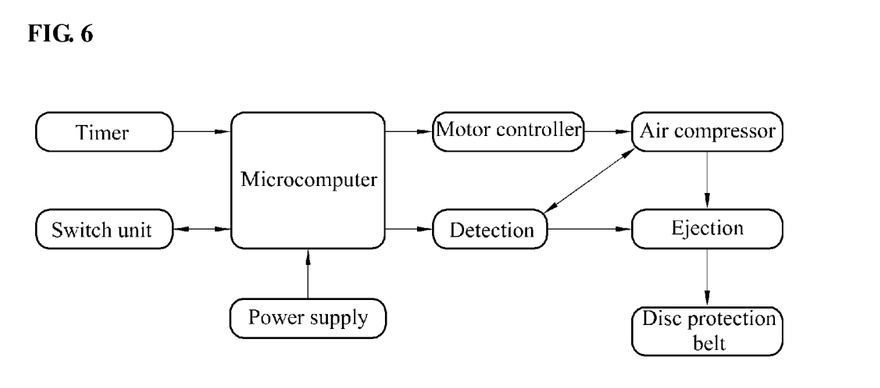
FIG. 6 is a block diagram showing a configuration of the present invention.

Next, FIG. 4 is a view showing a state in which the waist support with the disc protection belt according to the embodiment of the present invention is worn at the waist of the human body.

Referring to FIG. 4, the disc protection belt 200 is coupled to the panel 110 through the bolt hole 120 from outside the panel 110, both ends of the disc protection belt 200 enter the panel 110 through the pair of first openings 130 and then exit the panel 110 through the pair of second openings 140, and the waist support 100 with the disc protection belt 200 is worn at the waist of the human body 300.

Accordingly, the disc protection belt 200 can extend the backbone of the human body 300, and can strongly pull the waist.

As shown in FIGS. 5~11, the configuration of the present invention includes the disc protection belt 200 expanded by injection of air, an air pump 10 configured to inject air into the disc protection belt 200, and an air control unit 21 configured to remove air injected into the disc protection belt 200 by the air pump 10.

Here, an ejection port 11 of the air pump 10 is connected to an air injection port 101 of the disc protection belt 200 to inject air into the disc protection belt 200, and the air control unit 21 is formed at the ejection port 11 of the air pump 10 to discharge air injected through the air injection port 101 of the disc protection belt 200.

Here, the air pump 10 is automatically or manually operated by a controller 30 controlled by a microcomputer according to a user's selection through manipulation of a switch. In addition, injection and discharge of air can be performed at predetermined time intervals according to information input by a user or according to a predetermined method. Of course, such a controller can uniformly maintain a pressure of injected air.

Further, in the waist support 100, air filling the disc protection belt 200 can be discharged by the air control unit 21 installed in the ejection port 11 of the air pump 10. As a discharge port 20 branches off from the ejection port 11 and the air control unit 21 is installed at the discharge port 20, the air control unit 21 is operated by operation of the air pump 10 or the controller 30 connected to the air pump 10 to enable easy injection and discharge of injected air.

Furthermore, the discharge port 20 having a separate air control unit 21 may be installed at the air injection port 101 of the disc protection belt 200 such that a user can arbitrarily manipulate the air control unit 21 to discharge air or induce discharge of air. Here, a detection unit configured to detect discharge of air may be installed at the air pump 10 or may be manually operated to inject air again.

In addition, the disc protection belt vertically extending by injection of air includes an air bag formed by adhering overlapped synthetic resin sheets at predetermined intervals, and the air bag includes an elastic member so that the air bag can vertically extend by injection of air and can contract by discharge of air.

When the overlapped synthetic resin sheets are used, air can be easily injected.

Figure 7:
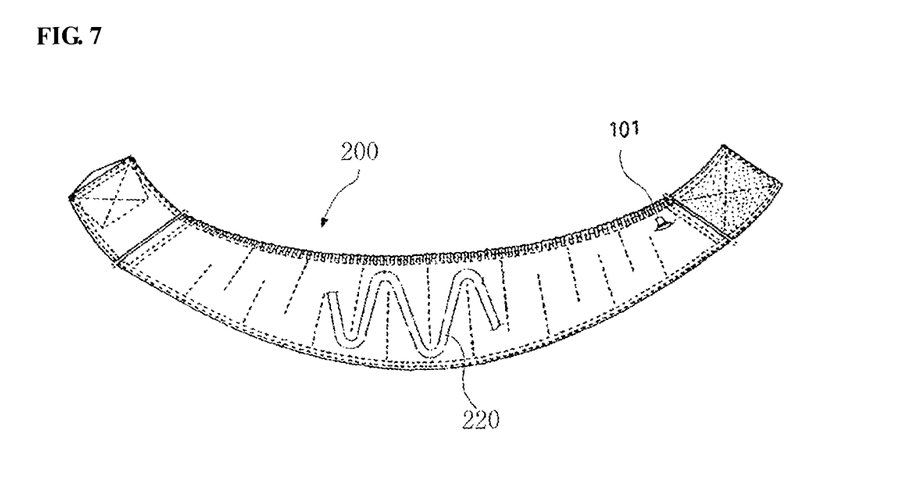
FIGS. 7 and 8 are exploded perspective views showing another structure of a disc protection belt.
Figure 8:
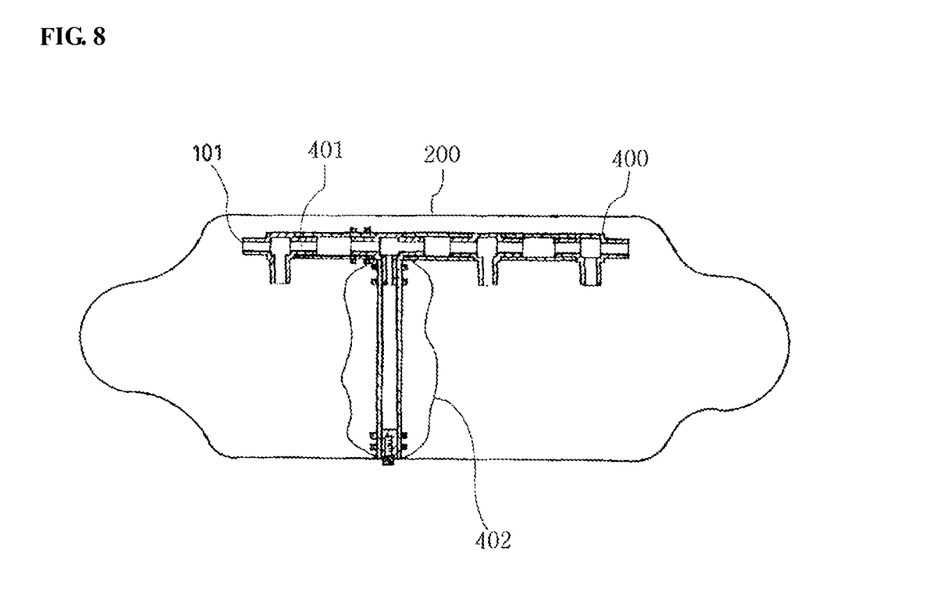
Figure 9:
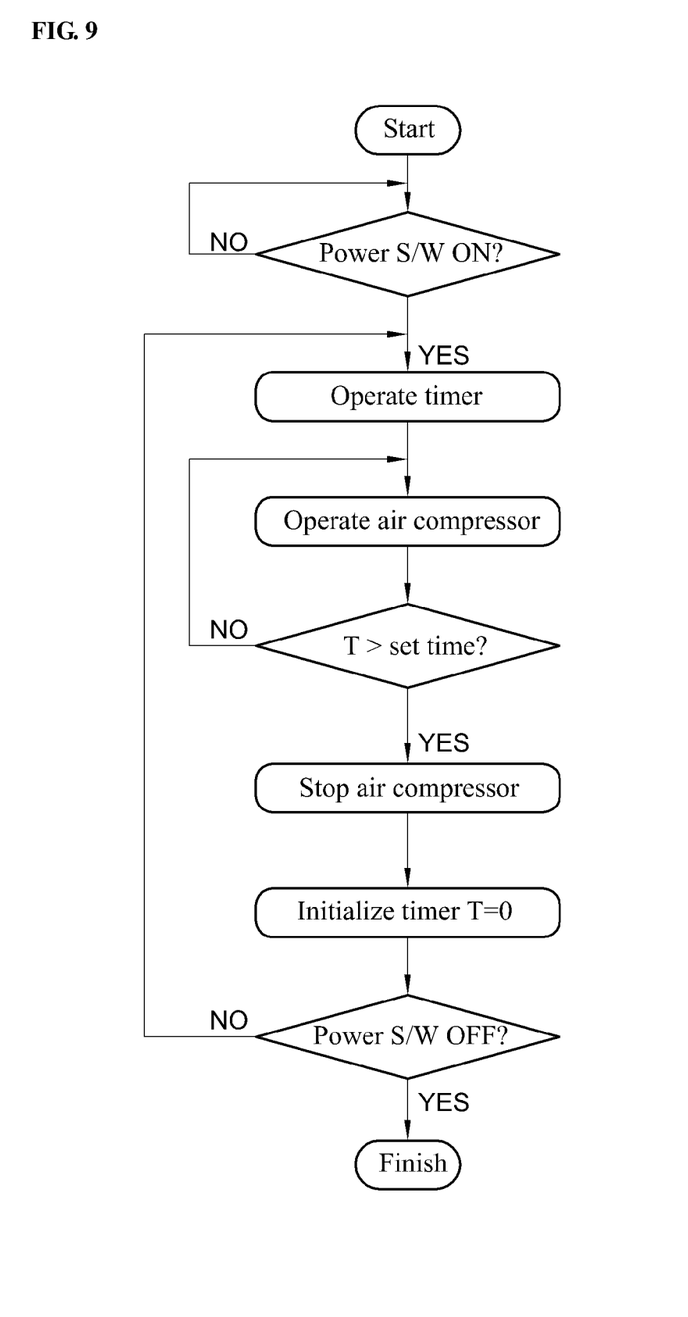
FIG. 9 is a flowchart showing an embodiment of an air control unit of the present invention.
Figure 10:
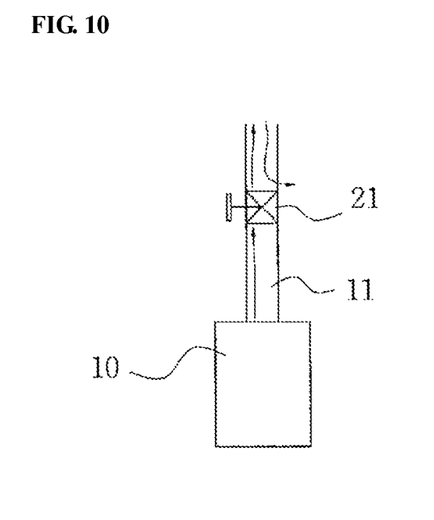
FIGS. 10 and 11 are schematic views showing another configuration of the air control unit.
Figure 11:
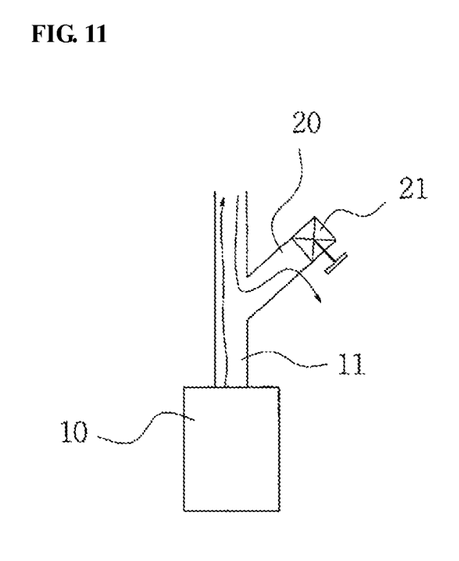

However, when the disc protection belt includes an elastic hose 220 formed of a material having characteristics like rubber, the elastic hose 220 may be formed in a zigzag or separate elastic hoses 220 may be connected to upper and lower portions of a connector 400 having a flow path 401. When the elastic hose 220 is applied to the disc protection belt including a pocket 402 configured to receive the expanded elastic hose 220, a branch pipe may be formed at the ejection port of the air pump to increase a capacity or an instant pressure of the air pump, enabling injection of air at a high pressure.

Accordingly, as the pulled waist is maintained for a certain time and then released at predetermined intervals, the vertebra and muscles around the vertebra can be relaxed to enhance treatment of the disc.

As a result, when a user does not go out, the air pump is operated to repeat injection and discharge of air to obtain a physical therapy effect like in a clinic, and when a user goes out, the pulled waist can be maintained to protect the user's waist.

As can be seen from the foregoing, the waist support with a disc protection belt having functions of strongly pulling and fixing the waist as well as extending the backbone can be provided.

While the invention has been shown and described with reference to certain example embodiments thereof, it will be understood by those skilled in the art that various changes in form and details may be made therein without departing from the spirit and scope of the invention as defined by the appended claims.

What is claimed is:

1. A waist support formed to conform to the waist of the human body, which comprises:
   a panel formed to conform to the waist of the human body; and
   a disc protection belt coupled to the panel by a bolt,
   wherein the panel comprises:
   a support section disposed to correspond to a backbone;
   a bolt hole formed in the support section to be coupled to the disc protection belt by the bolt;
   a pair of first openings formed in left and right sides of the support section with the bolt hole interposed therebetween; and
   a pair of second openings spaced out a predetermined distance from the bolt hole with the first openings interposed therebetween,
   the disc protection belt is coupled to the panel through the bolt hole from outside the panel, and both ends of the disc protection belt enter the panel through the pair of first openings and then exit the panel through the pair of second openings,
   the panel further comprises a pair of third openings disposed between the pair of first openings and the pair of second openings, and
   the third openings have center portions narrower than upper and lower portions thereof.

2. The waist support according to claim 1, wherein a width of the support section is gradually reduced toward a center thereof and the bolt hole is formed in the center of the support section.

3. The waist support according to claim 1, wherein the panel has an outside formed of an acrylonitrile butadiene styrene (ABS) material and an inside formed of a polyethylene (PE) or sponge material.

4. The waist support according to claim 2, wherein the panel has an outside formed of an acrylonitrile butadiene styrene (ABS) material and an inside formed of a polyethylene (PE) or sponge material.

* * * * *